(12) United States Patent
Jordan et al.

(10) Patent No.: US 11,351,322 B2
(45) Date of Patent: Jun. 7, 2022

(54) GEL RESUSCITATION MASK

(71) Applicant: Fisher & Paykel Healthcare Limited, Auckland (NZ)

(72) Inventors: Kenneth Gary Jordan, Auckland (NZ); Erik Robertus Scheirlinck, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 583 days.

(21) Appl. No.: 15/126,824

(22) PCT Filed: Mar. 17, 2015

(86) PCT No.: PCT/NZ2015/050027
§ 371 (c)(1),
(2) Date: Sep. 16, 2016

(87) PCT Pub. No.: WO2015/142191
PCT Pub. Date: Sep. 24, 2015

(65) Prior Publication Data
US 2017/0087321 A1    Mar. 30, 2017

Related U.S. Application Data

(60) Provisional application No. 61/954,760, filed on Mar. 18, 2014.

(51) Int. Cl.
*A61M 16/06*    (2006.01)
(52) U.S. Cl.
CPC ........ *A61M 16/0605* (2014.02); *A61M 16/06* (2013.01); *A61M 2205/0216* (2013.01); *A61M 2240/00* (2013.01)

(58) Field of Classification Search
CPC .......... A61M 16/0605; A61M 16/0616; A61M 16/0627; A61M 16/0644; A61M 16/06;
(Continued)

(56) References Cited

U.S. PATENT DOCUMENTS 5,074,297 A    12/1991  Venegas
5,146,914 A  *  9/1992  Sturrock ............... A61M 16/06
                                          128/202.29
(Continued)

FOREIGN PATENT DOCUMENTS

CN    101389369    3/2009
CN    101732787    6/2010
(Continued)

OTHER PUBLICATIONS

Extended European Search report for Application No. 15764690.2 dated Oct. 25, 2017 in 7 pages.
(Continued)

*Primary Examiner* — Joseph D. Boecker
*Assistant Examiner* — Brian T Khong
(74) *Attorney, Agent, or Firm* — Knobbe Martens Olson & Bear, LLP

(57) ABSTRACT

A neonatal resuscitation mask that achieves an effective seal with a patient's face with minimal application forces. The mask can include a cushion that forms a sealing surface with a patient's face that is made from a soft gel material. The cushion can also include a restriction ring that is capable of limiting radial expansion and collapse of the cushion, when application forces are applied.

21 Claims, 5 Drawing Sheets

(58) Field of Classification Search
CPC ...... A61M 16/0611; A61M 2016/0661; A61M 2205/0216; A61M 2205/0266; A61M 2240/00; E03C 1/308
See application file for complete search history.

(56) References Cited

U.S. PATENT DOCUMENTS

| | | | |
|---|---|---|---|
| 5,660,174 A * | 8/1997 | Jacobelli | A61M 16/06 128/206.21 |
| 6,035,852 A * | 3/2000 | Hoftman | A61M 16/06 128/206.21 |
| 7,185,653 B2 | 3/2007 | Lee | |
| 7,523,754 B2 * | 4/2009 | Lithgow | A61M 16/06 128/206.24 |
| 8,042,542 B2 | 10/2011 | Ging et al. | |
| 8,069,855 B2 | 12/2011 | Chang | |
| 8,393,324 B1 * | 3/2013 | Saad | A61M 16/06 128/206.21 |
| 2002/0040515 A1 | 4/2002 | Uehara et al. | |
| 2002/0073934 A1 * | 6/2002 | Barney | A61M 16/06 119/831 |
| 2003/0168063 A1 * | 9/2003 | Gambone | A61M 16/0633 128/203.16 |
| 2004/0144386 A1 * | 7/2004 | Frater | A61M 16/0683 128/206.24 |
| 2006/0042629 A1 | 3/2006 | Geist | |
| 2006/0118118 A1 * | 6/2006 | Smaldone | A61M 16/0616 128/206.21 |
| 2007/0125384 A1 * | 6/2007 | Zollinger | A61M 16/06 128/206.24 |
| 2007/0272169 A1 * | 11/2007 | Barney | A61M 16/0825 119/831 |
| 2008/0289633 A1 * | 11/2008 | Kwok | A61M 16/06 128/206.24 |
| 2008/0302366 A1 * | 12/2008 | McGinnis | A61M 16/0633 128/206.24 |
| 2009/0000623 A1 * | 1/2009 | Lynch | A61M 16/06 128/206.24 |
| 2009/0139525 A1 * | 6/2009 | Schirm | A61M 16/0605 128/205.25 |
| 2009/0250061 A1 * | 10/2009 | Marasigan | A61B 5/6803 128/205.13 |
| 2010/0012128 A1 * | 1/2010 | Takishita | A61M 16/06 128/206.24 |
| 2010/0101581 A1 * | 4/2010 | Lang | B29C 65/7847 128/205.25 |
| 2010/0313891 A1 * | 12/2010 | Veliss | A61M 16/0622 128/206.26 |
| 2011/0088699 A1 * | 4/2011 | Skipper | A61M 16/06 128/206.26 |
| 2011/0146684 A1 * | 6/2011 | Wells | A61M 16/06 128/205.25 |
| 2011/0174310 A1 * | 7/2011 | Burz | A61M 16/0622 128/206.24 |
| 2011/0220114 A1 | 9/2011 | Lithgow et al. | |
| 2012/0216819 A1 | 8/2012 | Raje et al. | |
| 2012/0312304 A1 | 12/2012 | Lynch et al. | |
| 2012/0318272 A1 * | 12/2012 | Ho | A61M 16/0616 128/205.25 |
| 2013/0008449 A1 | 1/2013 | Busch et al. | |
| 2013/0014760 A1 * | 1/2013 | Matula, Jr. | A61M 16/06 128/205.25 |
| 2013/0220327 A1 | 8/2013 | Barloe et al. | |
| 2014/0166018 A1 | 6/2014 | Dravitzki et al. | |
| 2014/0366886 A1 * | 12/2014 | Chodkowski | A61M 16/06 128/206.24 |
| 2015/0144140 A1 * | 5/2015 | Eury | A61M 16/06 128/206.24 |

FOREIGN PATENT DOCUMENTS

| | | |
|---|---|---|
| CN | 101861180 | 10/2010 |
| CN | 101965209 | 2/2011 |
| CN | 101987221 | 3/2011 |
| CN | 102834138 | 12/2012 |
| CN | 103118732 | 5/2013 |
| CN | 103354752 | 10/2013 |
| CN | 103517730 | 1/2014 |
| CN | 106573122 | 4/2017 |
| DE | 20 2014 104150 U1 | 9/2014 |
| EP | 2 145 645 | 1/2010 |
| WO | WO 2006/074514 | 7/2006 |
| WO | WO 2013/084109 A1 | 6/2013 |
| WO | WO 2013/175409 | 11/2013 |
| WO | WO 2015/142191 | 9/2015 |

OTHER PUBLICATIONS

International Search Report; PCT/NZ2015/050027; dated May 28, 2015; 7 pages.
European Examination Report for Application No. 15764690.2 dated May 3, 2019, 4 pages.
Chinese Second Office Action for Application No. 201580008618.5 dated Apr. 10, 2019 19 pages.
Australian Examination Report for Application No. 2015232049 dated Jan. 8, 2019, 4 pages.
Examination Report in Australian Application No. 2015232049 dated Dec. 13, 2019 in 3 pages.
Australian Examination Report for Application No. 2020201718 dated Jul. 23, 2020, 5 pages.
European Examination Report for Application No. 20166610.4 dated Jul. 15, 2020, 23 pages.
Chinese Third Office Action for Application No. 201580008618.5 dated Sep. 24, 2019, 10 pages.
Chinese Fourth Office Action for Application No. 201580008618.5 dated Sep. 18, 2020, 6 pages.
European Examination Report for Application No. 20204090.3 dated Mar. 18, 2021, 5 pages.

* cited by examiner

GEL RESUSCITATION MASK

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

The present disclosure generally relates to resuscitation masks. More particularly, the present disclosure relates to a neonatal resuscitation mask with a sealing component made from a gel material.

It is common for newborn human babies to require some assistance to begin breathing at birth. If breathing cannot be induced by clearing the patient's airways and providing some stimulation then ventilation may be required. One common approach for providing ventilation to neonates is to apply positive pressure to the patient's airways via a mask that forms a seal around the nose and mouth. Neonatal resuscitation masks are usually round or elliptical in shape and come in a range of sizes that can cater for babies of differing sizes. Typically these masks will include a cushioned rim that is intended to enable a seal to be created between the mask and face of the patient. The cushioned rim may be formed in a number of ways. Two common forms include a seal with an inflatable portion that is inflated by an external air supply, and a thin membrane surface that is capable of at least partially deforming to match the patient's facial geometry.

It is important for the efficacy of the treatment that an effective seal is achieved between the mask and the patient's face. If leaks occur then the pressures applied to the airways may not be sufficient for resuscitation. In order to achieve a seal with the patient's face a force is applied to the mask in order to make the sealing surface conform to the facial geometry. Since the masks typically have minimal curvature in the sealing surface, to match facial geometries, it may be necessary for medical practitioners to apply substantial forces to the mask and thus the patient's face to achieve a seal. The application of excessive pressure forces to a baby's face can have a variety of negative side-effects. Some of the side-effects can include tissue and structural damage to the face, and in some instances blockage of airways and Bradycardia (slowing of the heart) can occur. These side-effects are undesirable and compromise the ongoing health of the patient.

It is an object of certain embodiments disclosed herein to provide an improved or alternative mask that might overcome or ameliorate problems with existing masks, or at least provide the public with a useful choice.

SUMMARY

The present disclosure includes a sealing cushion for a neonatal resuscitation mask, which seeks to provide an improved seal with a patient's face, whilst reducing the amount of application force required to achieve said seal. Reducing the forces required to achieve an effective seal with a patient's face may have the advantage of minimizing or avoiding any facial damage and or negative side-effects to the patient. A more effective and easily achieved seal between the patient and mask may also improve the efficacy of the treatment being provided and reduce any delays in providing the therapy. The sealing cushion can be made from an unskinned gel material, which can provide adhesive and deformation properties that aide in creating an effective seal between the mask and the patient.

Disclosed is a mask for the delivery of breathable gases to a subject, the mask comprising a cushion and one or more restriction components,
    the cushion comprising a compressible gel material and having an outer perimeter and a sealing surface, the sealing surface being configured to form a seal around at least one airway of a patient in use, and
    the one or more restriction components extending at least partly around, or forming part of, the outer perimeter of the cushion, and reducing or limiting radial expansion or deformation of the cushion in use.

In various embodiments the cushion may comprise a compressible gel material having a first Shore hardness, and the one or more restriction components extend at least partly around, or form part of, the outer perimeter of the cushion spaced apart from the sealing surface, and comprise a material having a second Shore hardness, the second Shore hardness being greater than the first Shore hardness.

Disclosed is a resuscitation mask comprising a frame, a cushion, and one or more restriction components,
    the cushion comprising a compressible gel material having a first Shore hardness and having an outer perimeter, a frame end that engages the frame, and a sealing surface, the sealing surface being configured to form a seal around at least one airway of a patient, and
    the one or more restriction components extending at least partly around or forming part of the outer perimeter of the cushion spaced apart from the frame end and the sealing surface and comprising a material having a second Shore hardness, the second Shore hardness being greater than the first Shore hardness.

In various embodiments the gel material may have an adhesive surface.

Disclosed is a resuscitation mask comprising a frame, a cushion, and one or more restriction components,
    the cushion comprising a compressible gel material having an adhesive surface and a first Shore hardness, the cushion having an outer perimeter, a frame end that engages the frame, and a sealing surface, the sealing surface being configured to form a seal around at least one airway of a patient, and
    the one or more restriction components extending at least partly around or forming part of the outer perimeter of the cushion spaced apart from the frame end and the sealing surface and comprising a material having a second Shore hardness, the second Shore hardness being greater than the first Shore hardness.

In various embodiments the mask may be a nasal, oral, or oronasal mask.

In various embodiments the frame may comprise a connection port for attachment of a conduit.

In various embodiments the frame may be of a generally cylindrical, elliptical or asymmetric form.

In various embodiments the cushion may be generally cylindrical, elliptical or asymmetric.

In various embodiments the gel material may be unskinned.

In various embodiments the gel material may have an adhesive surface.

In various embodiments the sealing surface may be generally flat or curved to substantially match the geometry of a patient's face.

In various embodiments the mask may be symmetrical and can be applied in any orientation to the face of the patient.

In various embodiments the mask may comprise a visual alignment indicator on the outer surface of the mask.

In various embodiments the gel material may be a silicone rubber gel.

In various embodiments the sealing surface may be adhesive.

In various embodiments the sealing surface may be not adhesive.

In various embodiments the cushion may have a Shore hardness of about OO-5, OO-10, OO-15, OO-20, OO-25, OO-30, OO-35, OO-40, OO-45, or OO-50, and useful ranges may be selected between any of these values (for example, about OO-5 to about OO-50, about OO-15 to about OO-45, or about OO-25 to about OO-45). In various embodiments the Shore hardness of the cushion may be about OO-35.

In various embodiments the one or more restriction components may have a Shore hardness of at least about A-5, A-10, A-15, A-20, A-25, A-30, A-35, A-40, A-45, A-50, A-55, A-60, A-65, A-70, A-75, A-80, A-85, A-90, A-95, or A-100, or more, and useful ranges may be selected between any of these values (for example, about A-5 to about A-100, about A-10 to about A-100, about A-15 to about A-100, about A-5 to about A-75, about A-10 to about A-75, about A-15 to about A-75, about A-5 to about A-50, about A-10 to about A-50, about A-15 to about A-50, about A-10 to about A-30, or about A-15 to about A-25). In various embodiments the Shore hardness of the one or more restriction components may be about A-20.

In various embodiments the one or more restriction components may minimize radial expansion of the cushion in use.

In various embodiments the one or more restriction components may comprise one or more rings that minimize radial expansion of the cushion in use.

In various embodiments the one or more restriction components may comprise at least one inelastic or substantially rigid component that extends at least partly around the perimeter of the cushion.

In various embodiments the one or more restriction components may limit the ability of the cushion to expand and/or deform in a radial direction whilst still allowing deformation in a direction that is largely perpendicular to the face of a patient.

In various embodiments the cushion structure may allow greater deformation in the region of the cushion that is proximal to the patient's nose than there is in the region that is proximal to the chin.

In various embodiments the one or more restriction components may comprise a separate component that is attached to the exterior of the cushion.

In various embodiments the one or more restriction components may comprise a substantially rigid or non-elastic polymer.

In various embodiments the one or more restriction components may be attached to the cushion with an adhesive or by co-molding the one or more restriction components and the cushion.

In various embodiments the one or more restriction components may comprise a change in geometry that resists radial deformation of the cushion.

In various embodiments the one or more restriction components may comprise a thickening in the cross-section of the cushion.

In various embodiments the one or more restriction components may comprise at least one region of the cushion where the hardness of the cushion material has been varied.

In various embodiments the one or more restriction components may comprise a non-gel silicone rubber.

In various embodiments the one or more restriction components may be located approximately halfway along the length of the cushion.

In various embodiments the mask may comprise multiple restriction components.

In various embodiments the mask may comprise multiple restriction components in the form of substantially inelastic or rigid restriction rings positioned in series along the length of the cushion, and separated from each other by portions of soft, flexible material.

In various embodiments the radial thickness of the cushion may be at least about 1, 2, 3, 4, 5, 6, 7, 8, 9, 10, 11, 12, 13, 14, 15, 16, 17, 18, 19, or 20 mm, and useful ranges may be selected between and of these values (for example, about 1 to about 20, about 2 to about 20, about 3 to about 20, about 1 to about 10, about 2 to about 10, or about 2 to about 8 mm).

In various embodiments the radial thickness of the cushion may be about 4 to about 8, preferably about 6 mm.

In various embodiments the cushion may be substantially frustoconical and the sealing end smaller in diameter than the frame end.

In various embodiments the cushion may comprise two or more layers of different composition.

In various embodiments the cushion may comprise a first layer, a second layer, and a third layer, the first and third layers comprising a material having a first Shore hardness, and the second layer, situated between the first and third layers, comprising a material having a second Shore hardness, greater than the first Shore hardness.

In various embodiments the first and third layers may comprise a silicone gel.

In various embodiments the second layer may comprises a silicone rubber or thermoplastic elastomer.

In various embodiments the second layer may act as a restriction component.

In various embodiments the frame may be larger in diameter than the sealing surface of the cushion.

In various embodiments the cushion may comprise two or more layers acting as a restriction component and three or more soft deformable layers.

In various embodiments the first Shore hardness may be at least about or up to about OO-5, OO-10, OO-15, OO-20, OO-25, OO-30, OO-35, OO-40, OO-45, or OO-50, and useful ranges may be selected between any of these values (for example, about OO-5 to about OO-50, about OO-15 to about OO-45, or about OO-25 to about OO-45). In various embodiments the first Shore hardness may be about OO-35.

In various embodiments the second Shore hardness may be at least about A-5, A-10, A-15, A-20, A-25, A-30, A-35, A-40, A-45, A-50, A-55, A-60, A-65, A-70, A-75, A-80, A-85, A-90, A-95, or A-100, or more, and useful ranges may be selected between any of these values (for example, about A-5 to about A-100, about A-10 to about A-100, about A-15 to about A-100, about A-5 to about A-75, about A-10 to about A-75, about A-15 to about A-75, about A-5 to about A-50, about A-10 to about A-50, about A-15 to about A-50, about A-10 to about A-30, or about A-15 to about A-25). In various embodiments the second Shore hardness may be about A-20.

DETAILED DESCRIPTION OF PREFERRED EMBODIMENTS

Delivery of breathable gases to a patient typically involves the application of air pressure to a patient's airways via an interface or mask, including an oral mask, a nasal mask, or an oronasal (full face) mask. In order to deliver effective therapy to the patient a seal is established between the mask and the patient's face. To achieve this seal applying a substantial force to the mask and thus the patient's face is often observed, which may result in undesirable side effects for the patient. The present disclosure herein seeks to provide a mask for the delivery of breathable gases that is capable of sealing with a patient's face under minimal application forces, thus avoiding or minimizing any negative side effects that may occur.

Similarly, resuscitation of newborn babies typically involves the application of air pressure to a patient's airways via an interface or mask. In order to deliver effective therapy to the patient a seal is established between the mask and the baby's face. To achieve this seal applying a substantial force to the mask and thus the baby's face is often observed, which may result in undesirable side effects for the baby. The present disclosure herein seeks to provide a neonatal resuscitation mask that is capable of sealing with a baby's face under minimal application forces, thus avoiding or minimizing any negative side effects that may occur.

Whilst the disclosed mask is described in relation to the treatment of neonatal babies, as indicated above, it is possible that it may provide the same or similar benefits to patients of other ages for delivery of breathable gases, including but not limited to resuscitation applications. As such it is to be understood that when describing the function of the disclosed mask in relation to the treatment of a patient, the term 'patient' can relate to a person of any age from neonatal through to geriatric.

Figure 1:
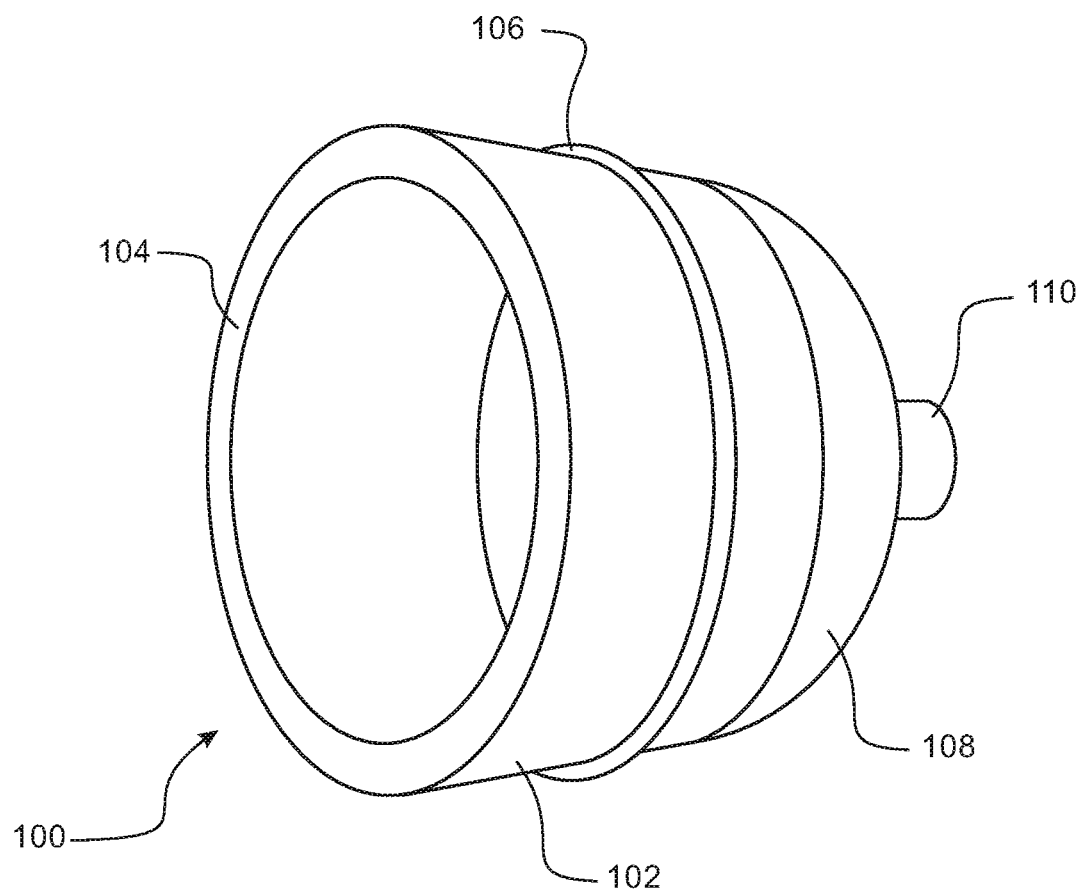
FIG. 1 shows a perspective view of the presently disclosed neonatal resuscitation mask.

FIG. 1 shows a perspective view of one embodiment of the mask 100. It shows that the mask 100 is of a generally cylindrical form. There is a face contacting cushion 102 with a sealing surface 104, a restriction ring 106, a frame portion 108, and a connection port 110 for attaching to a conduit, which is in turn attached to a ventilator device. The cushion 102 and sealing surface 104 are intended to contact and form a seal with a patient's face and can be made from a soft and compressible gel material, such as described herein. The sealing surface 104 is shown as generally flat; however in alternative embodiments it may have some curvature to better match the geometry of a patient's face. The cushion 102 is a generally cylindrical shape, however in other embodiments may be elliptical or asymmetric in shape. Cylindrical masks, including cylindrical masks that are symmetric have advantages in neonatal applications, particularly resuscitation applications because the face of a neonate is typically more symmetrical and less contoured than the face of a child, adolescent, or adult. One advantage of a mask that has a generally flat sealing surface 104 and a cylindrical cushion 102 is that it can be easier and quicker to fit to a patient. This is because the mask is symmetrical and the mask can be applied in any orientation, i.e. there is no requirement to align certain features of the mask with certain facial features of the patient. Cylindrical masks, including cylindrical masks that are asymmetric or elliptical may be used in applications where the face of the patient is less symmetric and more contoured than the face of a neonate, such as the face of a child, adolescent, or adult. For non-neonatal applications, a substantially cylindrical mask may be at least slightly asymmetric or elliptical. In such embodiments, including an embodiment where the sealing surface has a curvature to substantially match a patient's facial geometry; there can be a visual alignment indicator on the distal outer surface of the mask. This alignment indicator can be visible to a medical practitioner when they are fitting the mask to a patient. It will allow the practitioner to correctly orientate the mask for a quick and effective fit.

The cushion can be made from a gel material that can include but is not limited to silicone rubber gels. Gels can exhibit several properties which may be beneficial in improving the seal between the cushion and a patient's face. Firstly it is common for gels to have a tacky or adhesive surface. This property can be advantageous in maintaining a consistent connection between the sealing surface of the cushion and the patient's face. The adhesion forces between the cushion and the patient's skin may create an airtight seal and may also reduce the amount of application force required to maintain this connection and seal.

The use of gel materials is commonly known in the manufacture of cushions for a variety of respiratory masks that are used to provide patients with a range of respiratory therapies; including but not limited to non-invasive ventilation (NIV), oxygen therapy and constant positive airway pressure (CPAP) therapy. These masks typically have a skin or membrane that encases the gel material. This is to provide structure to a soft material and to minimize the adhesiveness of the surface. Adhesiveness can be an undesirable characteristic in traditional respiratory masks as a result of them being used for extended timeframes in a variety of environments. The adhesiveness can attract dirt making the cushion unhygienic and difficult to clean. Neonatal resuscitation masks are more likely to be single use or disposable and are used for relatively short timeframes, in comparison to other respiratory masks, and are used in substantially controlled environments. The nature of their use means that having an adhesive surface is not a significant risk to hygiene, as they are less likely to be exposed to contamination within the time and location of use. The mask can be packaged in such a way as to prevent contamination before use. In one embodiment the sealing surface can be adhesive to improve the sealing ability of the mask. In alternative embodiments it may be desirable for the sealing surface not to be adhesive.

Figure 2:
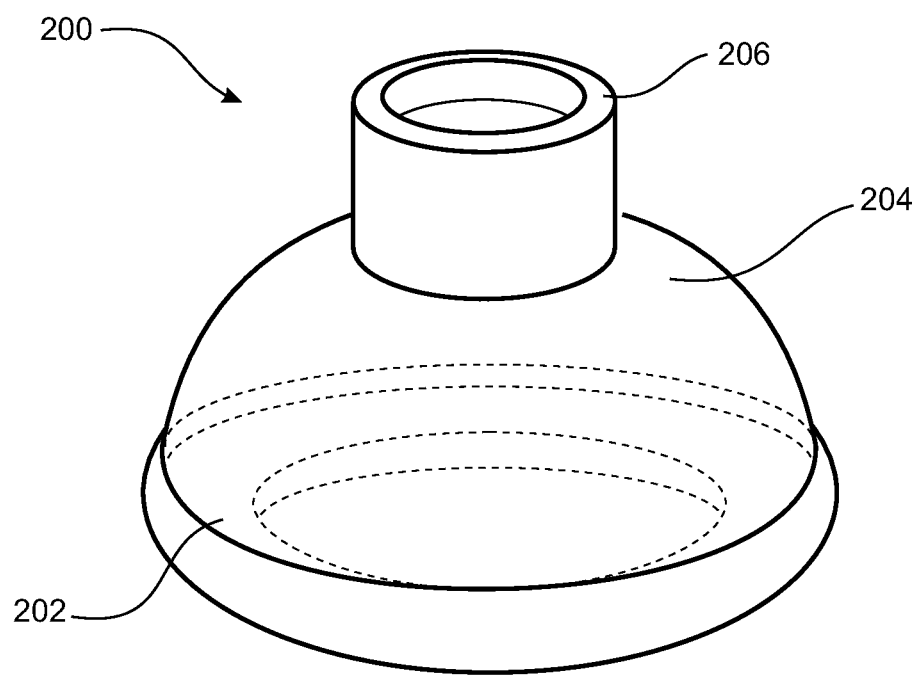
FIG. 2 shows an image of a neonatal resuscitation mask that is known in the art.

The gel material selected for the cushion 102 can have properties that allow it to readily change shape and thus conform more accurately to the patient's face than traditional neonatal resuscitation masks. FIG. 2 shows an image of a traditional neonatal mask 200 that is known in the art. It has a sealing surface 202, mask body 204 and an air supply attachment location 206. Traditionally neonatal masks often have a thin silicone sealing surface 202 that contacts the patient's face. The silicone sealing surfaces are typically flexible and capable of at least partially conforming to the patient's face. It is common, however, for the sealing surface to not be flexible enough to conform exactly to the small features of a baby's face, or alternatively for creases or folds to form in the sealing surface, both of which can result in leaks being generated. These leaks are often overcome by applying more force to the mask and thus the patient's face. The mask 100 can have a cushion made from a soft gel material, which can have a Shore hardness of about OO-5 to about OO-50, including about OO-35. This will encourage the cushion to conform more readily to the facial geometry of the patient, under lower application forces. The gel may be capable of more localized deformation than traditional silicone masks, which may improve the seal between the mask and the patient.

Figure 3A:
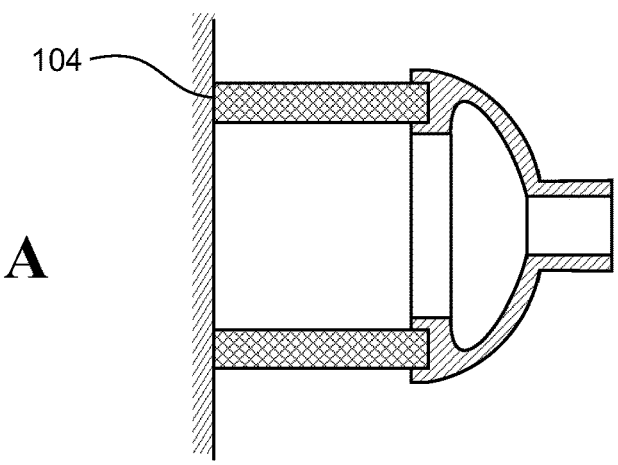
FIGS. 3a and b show cross-sectional views of a gel mask without a restriction ring, first in a neutral position and second with an excessive force applied to it.
Figure 3B:
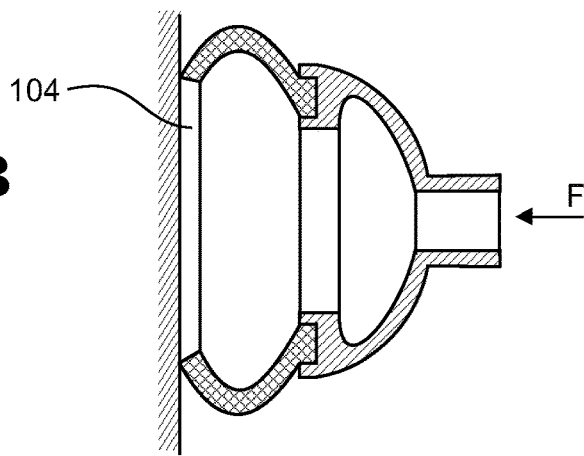
Figure 4:
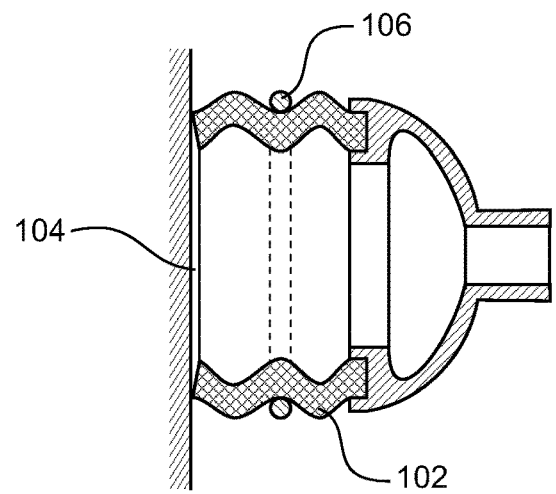
FIG. 4 shows a cross-sectional view of the presently disclosed mask.
Figure 5:
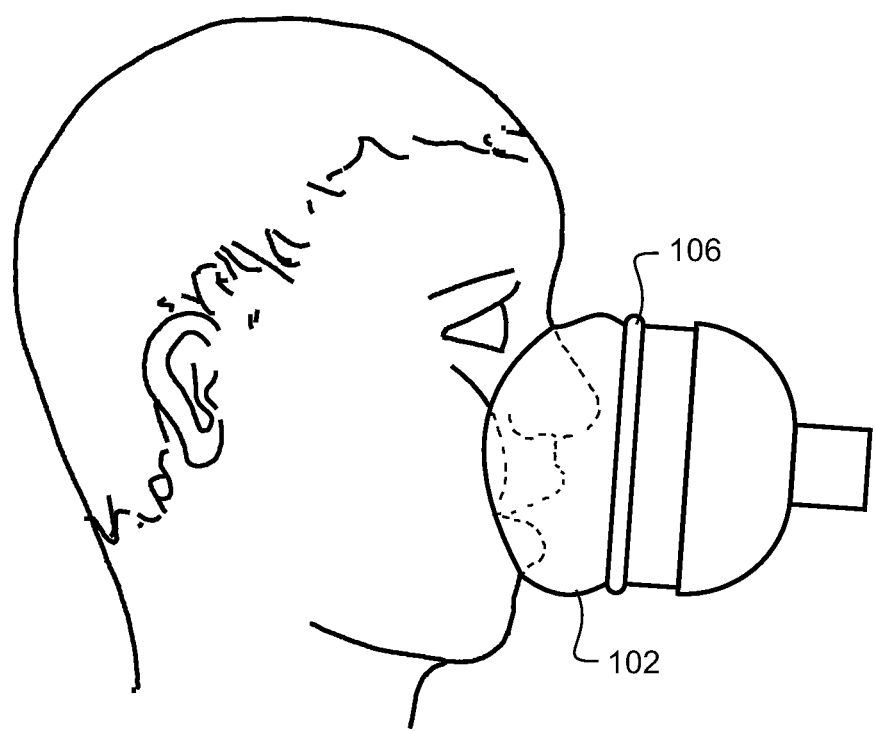
FIG. 5 shows a side view of the mask of the presently disclosed on a baby.

One side effect of using an unskinned gel, which is softer than traditional mask materials, is that the cushion component can be predisposed to collapsing if excessive forces are applied to it. This in turn can lift the sealing surface away from the patient's face, as shown in FIG. 3b, causing leaks and compromising the level of therapy that is delivered. FIGS. 3a and 3b show that when a force F is applied, in the direction shown, the sealing surface 104 may lift away from the face, resulting in smaller surface area coming into contact with the patient's face and creating a seal. One method of overcoming this problem is to provide a restriction ring 106 to the cushion 102 that minimizes radial expansion; one embodiment of which is shown in FIG. 1, and other embodiments in FIGS. 5 and 6. An inelastic or substantially rigid component 106 can extend around the perimeter of the sealing cushion 102. This component will limit the ability of the cushion to expand and/or deform in a radial direction whilst still allowing deformation in a direction that is largely perpendicular to the face of a patient. FIG. 4 shows a cross-sectional view of one embodiment of the disclosed mask when under a compressive force. It is shown that the cushion 102 can deform on either side of the restriction ring 106 with minimal deflection of the sealing surface 104. Deformation towards the nose and mouth of the patient is required in order to conform to the facial geometry of each individual. FIG. 5 shows how deformation of the seal may vary dependent on the facial geometries that are proximal to the various regions of the cushion 102. For instance there may be greater deformation in the region, of the cushion, that is proximal to the patient's nose than there is in the region that is proximal to the chin.

The restriction ring 106 may be formed in a number of ways. As is shown in the embodiments of FIGS. 1, 4, 5, and 6, the restriction ring can be a separate component that is attached to the exterior wall of the cushion 102. This component may be made from a substantially rigid or non-elastic polymer, such as a polymer having a Shore hardness of, for example, at least about A-5 to at least about A-100, or more, including about A-20. It can be secured in place by an adhesive or through co-molding techniques. In an alternative embodiment the restriction ring may not be a separate component. It may consist of a change in geometry that resists radial deformation of the cushion 102, such as a thickening in the cross-section of the cushion. Alternatively the restriction may be achieved through varying the hardness of the cushion material. For example if the cushion is to be made from a silicone rubber gel, then the restriction ring may be made from a non-gel silicone rubber with higher Shore hardness of, for example, about A-5 to about A-100, including about A-20. This may be applied to the cushion 102 through a co-molding process or any other suitable application process.

The restriction ring 106 can be located approximately halfway along the length of the cushion 102, as shown in FIGS. 1, 4, and 5. This will minimize any biasing of deformation of the cushion 102. If the restriction ring is located too close to the sealing surface 104 then it may limit deformation that is required for the sealing surface to conform to the facial geometry of the patient, thus compromising the ability of the mask 100 to seal and provide effective therapy. If the restriction ring 106 is too far from the sealing surface 104 then it may not be effective in its purpose of preventing radial expansion and collapse of the cushion 102. Expansion and collapse may occur between the sealing surface and the restriction ring. In an alternative embodiment there may be multiple restriction rings. The substantially inelastic or rigid restriction rings can be positioned in series along the length of the cushion, and separated from each other by portions of soft, flexible material.

As a result of using a soft gel material for the cushion 102 the wall thickness of the cushion becomes a significant factor in the masks ability to create an effective seal with the patient's face. The cushion 102 can have a tendency to inflate if an air-tight seal is achieved between the sealing surface 104 and the patient's face, and the wall thickness of the cushion 102 is too low. When inflation occurs, pressure builds up inside the mask 100 until a leak path is created and the seal between the cushion 102 and the patient's face is broken. This can make it difficult to maintain the seal required to provide effective therapy. Alternatively, depending on the strength of the adhesive forces between the sealing surface 104 and the patient's face, the buildup of pressure inside the mask 100 may result in a blow-out where a hole is formed in the wall of the cushion 102. Therefore the wall thickness may be selected to prevent inflation. A wall thickness of about 6 mm may be effective for a silicone rubber gel with a shore hardness of approximately OO-35. For materials of differing hardness a wall thickness of about 1 mm to about 20 mm may be suitable.

Figure 6A:
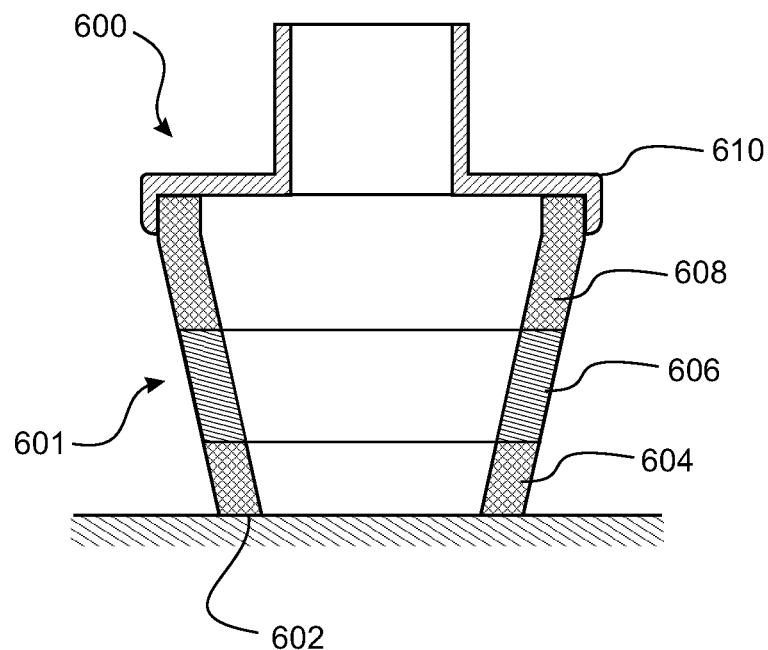
FIGS. 6a and 6b show cross-sectional views of an alternative mask embodiment, in a neutral position and with a force applied.
Figure 6B:
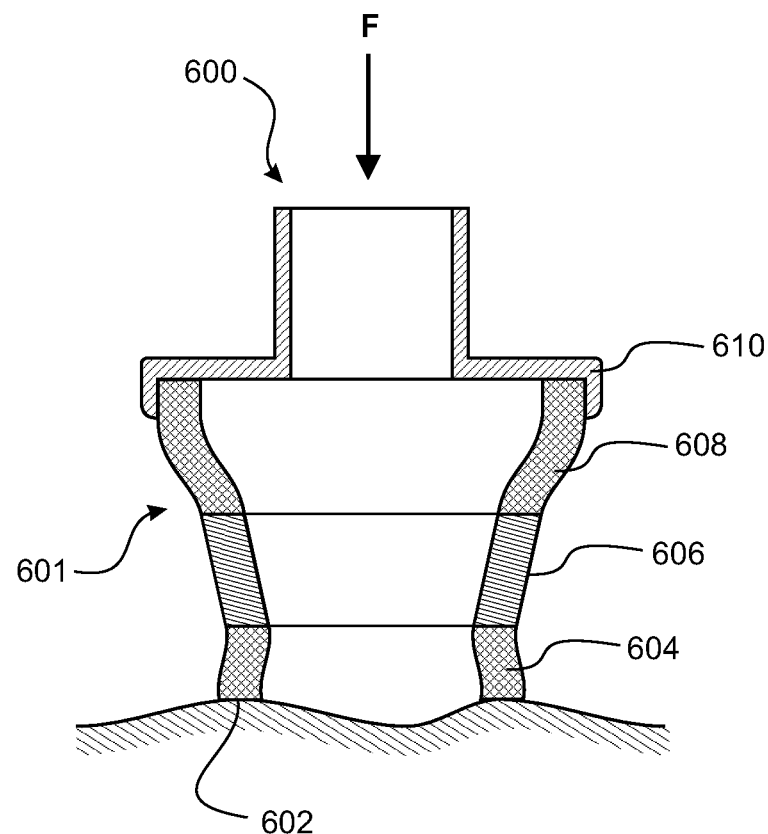

FIGS. 6a and 6b show an alternative embodiment of the disclosed mask. FIG. 6a shows the mask 600 in a neutral state, whilst FIG. 6b shows the same mask 600 with an axial force F applied in a direction towards the patient's face. The cushion 601 takes the form of a truncated cone, wherein the face contacting surface 602 is smaller in diameter than the distal end, and the cushion can be substantially circular or elliptical when viewed end on.

The cushion 601 can be configured to include layers of differing materials. In the embodiment shown there are a first layer 604 and a third layer 608, of a soft gel material, and a second layer 606, situated between the first and third layers, of harder more inelastic material. The soft layers 604 and 608 can be made from a silicone gel or other suitable material, such as described above. The second, more rigid, layer can be made from a silicone rubber, thermoplastic elastomer or other suitable material that provides some flexibility whilst maintaining a largely inelastic structure, such as described above. The second layer 606 acts as a restriction ring. As described previously, the restriction ring limits radial expansion of the cushion. The cushion retainer or frame 610 also provides some restriction to radial expansion, since it is larger in diameter than the face contacting ends of the cushion layers any deformation is substantially constrained within the diameter of the cushion retainer 610, as shown in FIG. 6b.

The layers of different material can have the effect of behaving in the manner similar to that of a concertina, wherein the soft layers 604 and 608 are compressible and the restriction ring 606 resists deformation and translates position. The first soft, flexible gel layer 604 can deform to substantially conform to the facial geometry of the patient. The first and third layers 604 and 608 can deform relative to the restriction ring 606 and the cushion retainer 610 in a manner that absorbs some of the application forces. This results in the cushion 600 compressing in an axial direction and expanding radially in a controlled way that is limited by the geometry of the restriction ring 606 and cushion retainer 610. In other embodiments there may be more than one restriction ring layer and more than two soft deformable layers. The first layer 604 may include an adhesive face contacting surface 602, to improve the sealing ability of the cushion, in some embodiments.

The conical geometry of the cushion 601 can be beneficial in that it helps to disperse the forces that are applied to the patient's face when the mask is applied. In an embodiment where the cushion 601 is circular; due to the changing diameter of the cushion any application forces F are spread over a varying cross-sectional area which causes the forces to be dispersed. The combination of the conical geometry, the soft material of the third layer 608 and the restriction ring 606 results in the application forces F being dispersed by the deformation of the third layer 608 before they are transferred to the patient's face. This is beneficial as it can reduce the amount of force applied to a patient's face and thus minimize the occurrence of facial damage.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to neonatal resuscitation. However, certain features, aspects and advantages of the use of the mask as described may be advantageously be used with other therapeutic or non-therapeutic systems requiring a seal about an airway of a patient. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A mask for the delivery of breathable gases to a subject, the mask comprising a cushion and one or more restriction components,
the cushion comprising an outer perimeter and a sealing surface, the sealing surface being configured to form a seal around at least one airway of the subject in use, wherein the sealing surface includes a tacky surface,
the one or more restriction components forming part of the outer perimeter of the cushion, and reducing or limiting radial expansion or deformation of the cushion in use,
wherein the cushion comprises a first layer, a second layer, and a third layer, the first and third layers comprising a compressible gel material having a first Shore hardness, the second layer situated between the first and third layers, the second layer comprising a material having a second Shore hardness, the second Shore hardness greater than the first Shore hardness,
wherein the cushion tapers from the third layer to the first layer so as to form a substantially frustoconical shape wherein the sealing surface is circular,
wherein the cushion is an unskinned gel, the unskinned gel is configured to be in direct contact with the face of the subject,
wherein the second layer of the cushion forms at least one of the one or more restriction components, and
wherein the mask is configured for neonatal use.

2. The mask of claim 1 wherein the one or more restriction components extend at least partly around, or form part of, the outer perimeter of the cushion spaced apart from the sealing surface, the one or more restriction components comprising the material having the second Shore hardness.

3. The mask of claim 2 wherein the unskinned gel has an adhesive surface.

4. The mask of claim 1 wherein the mask is a nasal, oral, or oronasal mask.

5. The mask of claim 1 wherein the sealing surface is generally flat or is curved to substantially match the geometry of a face of the subject, or wherein the mask is symmetrical and can be applied in any orientation to the face of the subject.

6. The mask of claim 1 wherein the gel material is a silicone rubber gel.

7. The mask of claim 1 wherein the cushion has a Shore hardness of OO-5 to OO-50.

8. The mask of claim 1 wherein the one or more restriction components have a Shore hardness of at least A-5 to A-100.

9. The mask of claim 1 wherein the one or more restriction components comprises one or more rings that minimize radial expansion of the cushion in use.

10. The mask of claim 1 wherein the one or more restriction components limits expansion and/or deformation of the cushion in a radial direction whilst still allowing deformation in a direction that is perpendicular to the face of the subject.

11. The mask of claim 1 wherein the cushion allows greater deformation in a region of the cushion that is proximal to a nose of the subject than in a region that is proximal to the chin.

12. The mask of claim 1 wherein the one or more restriction components:
(1) comprise a substantially rigid or non-elastic polymer, and/or
(2) are attached to the cushion with an adhesive or through co-molding techniques, and/or
(3) comprise a change in geometry that resists radial deformation of the cushion, and/or
(4) comprise a thickening in a cross-section of the cushion, and/or (5) comprise at least one region of the cushion where a hardness of the cushion has been varied, and/or
(6) comprise a non-gel silicone rubber, and/or
(7) are located halfway along a length of the cushion.

13. The mask of claim 1 wherein the one or more restriction components comprises multiple restriction components, the multiple restriction components comprising substantially inelastic or rigid restriction rings positioned in series along a length of the cushion, and separated from each other by portions of soft, flexible material.

14. The mask of claim 1 wherein a radial thickness of the cushion is at least 2 to 20 mm.

15. The mask of claim 1 wherein the first and third layers comprise a silicone gel and the second layer comprises a silicone rubber or thermoplastic elastomer.

16. A mask for the delivery of breathable gases to a subject, the mask comprising a frame, a cushion, and one or more restriction components,
the cushion comprising an outer perimeter, a frame end that engages the frame, and a sealing surface, the sealing surface being configured to form a seal around at least one airway of the subject, wherein the sealing surface includes a tacky surface, and
the one or more restriction components extending at least partly around or forming part of the outer perimeter of the cushion spaced apart from the frame end and the sealing surface, wherein the cushion comprises a first layer, a second layer, and a third layer, the first and third layers comprising a compressible gel material having a first Shore hardness, the second layer situated between the first and third layers, the second layer comprising a material having a second Shore hardness, the second Shore hardness greater than the first Shore hardness,
wherein the cushion is an unskinned gel, the unskinned gel in direct contact with the face of the subject,
wherein the one or more restriction components form a waist in the cushion when a force is applied to the cushion,
wherein the sealing surface has a smaller diameter than the frame end, and
wherein the mask is configured for neonatal use.

17. The mask of claim 16 wherein the sealing surface is smaller in diameter than the frame end.

18. The mask of claim 16 wherein the frame is larger in diameter than the sealing surface of the cushion.

19. A neonatal mask for the delivery of breathable gases to a subject, the neonatal mask comprising:
a cushion comprising an outer perimeter and a sealing surface, the sealing surface configured to form a seal around at least one airway of the subject in use;
one or more restriction components forming part of the outer perimeter of the cushion, and reducing or limiting radial expansion or deformation of the cushion in use;
wherein the cushion comprises a first layer, a second layer, and a third layer, the first and third layers comprising a compressible gel material having a first Shore hardness, the second layer situated between the first and third layers, the second layer comprising a material having a second Shore hardness, the second Shore hardness greater than the first Shore hardness,
wherein the cushion has a circular cross-section, and
wherein the cushion is an unskinned gel, the unskinned gel in direct contact with the face of the subject.

20. The neonatal mask of claim 19, wherein the cushion is cylindrical.

21. The neonatal mask of claim 20, wherein the mask further comprises a dome-shaped frame.

* * * * *